(12) United States Patent
Li et al.

(10) Patent No.: US 10,072,051 B2
(45) Date of Patent: Sep. 11, 2018

(54) ANTI-INFLAMMATORY LIPOPEPTIDE AND PREPARING METHOD AND APPLICATION THEREOF

(71) Applicant: EAST CHINA NORMAL UNIVERSITY, Shanghai (CN)

(72) Inventors: Dongqing Li, Shanghai (CN); Yue Wang, Shanghai (CN); Hongquan Li, Shanghai (CN); Yuping Lai, Shanghai (CN)

(73) Assignee: EAST CHINA NORMAL UNIVERSITY, Shanghai (CN)

( * ) Notice: Subject to any disclaimer, the term of this patent is extended or adjusted under 35 U.S.C. 154(b) by 194 days.

(21) Appl. No.: 14/440,291

(22) PCT Filed: Nov. 23, 2012

(86) PCT No.: PCT/CN2012/085171
§ 371 (c)(1),
(2) Date: May 1, 2015

(87) PCT Pub. No.: WO2014/012312
PCT Pub. Date: Jan. 23, 2014

(65) Prior Publication Data
US 2015/0274785 A1    Oct. 1, 2015

(30) Foreign Application Priority Data
Jul. 20, 2012 (CN) .......................... 2012 1 0254311

(51) Int. Cl.
| | | |
|---|---|---|
| A61K 38/00 | (2006.01) | |
| A61P 17/00 | (2006.01) | |
| A61P 29/00 | (2006.01) | |
| A61K 38/04 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 14/31 | (2006.01) | |
| C07K 1/107 | (2006.01) | |

(52) U.S. Cl.
CPC ............ C07K 14/31 (2013.01); C07K 1/1077 (2013.01); *A61K 38/00* (2013.01)

(58) Field of Classification Search
CPC ....... A61K 38/00; C07K 14/31; C07K 1/1077
See application file for complete search history.

(56) References Cited

FOREIGN PATENT DOCUMENTS

CN          102659932 A  *  9/2012  ............. C07K 14/31

OTHER PUBLICATIONS

Cogen et al., J. of Investigative Dermatology, Jan. 2010, 130(1), 192-200.*
Anonymous. Dissertation "The Molecular Mechanisms by Which Lipopeptides of *Staphylococcus* Epidermidis Protect from Microbial Infection and Regulate Inflammatory Responses in Skin Wounds" 2014.*
Li and Yai "Staphylococcal lipopeptide induces beta-cantenin to suppress TLR3-mediated skin inflammation in diabetes" J. Investigative Dermatology 137(5) Supplement 1, S99. May 2017.*
Li et al. "A Novel Lipopeptide from Skin Commensal Activates TLR2/CD36-p38 MAPK Signaling to Increase Antibacterial Defense against Bacterial Infection" Plos One 8(3): e58288. Published Mar. 5, 2013.*
Malina and Shai "Conjugation of fatty acids with different lengths modulates the antibacterial and antifungal activity of a cationic biologically inactive peptide" Biochem. J. 390:695-702. Published 2005.*

* cited by examiner

*Primary Examiner* — Christina Bradley
*Assistant Examiner* — Zachary J Miknis
(74) *Attorney, Agent, or Firm* — Birch, Stewart, Kolasch & Birch, LLP

(57) ABSTRACT

Disclosed is an anti-inflammatory lipopeptide, which comprises peptide chains and aliphatic chains, the peptide chain being linked to the aliphatic chain through a peptide bond, and an aliphatic acid being linked to the N-terminus of the peptide chain. The lipopeptide suppresses inflammatory response induced by poly(I:C), so as to prevent inflammation after skin injury and alleviate inflammatory response of skin inflammation such as allergic dermatitis. Also disclosed is a preparing method of the lipopeptide.

6 Claims, 10 Drawing Sheets
Specification includes a Sequence Listing.

ANTI-INFLAMMATORY LIPOPEPTIDE AND PREPARING METHOD AND APPLICATION THEREOF

REFERENCE TO SEQUENCE LISTING SUBMITTED VIA EFS-WEB

This application includes an electronically submitted sequence listing in .txt format. The .txt file contains a sequence listing entitled "2016-10-24 6075-0112PUS1 ST25.txt" created on Oct. 24, 2016 and is 778 bytes in size. The sequence listing contained in this .txt file is part of the specification and is hereby incorporated by reference herein in its entirety.

FIELD OF THE INVENTION

The present invention is related to the technology of biological engineering. More specifically, said invention is related to a lipopeptide used for suppressing the excessive inflammation, preparation methods and application thereof.

BACKGROUND

The inflammatory response characterized by red, swelling, heat, pain and dysfunction, is a protective response of the body against external injury. Appropriate inflammatory response is required for protecting hosts from external insults, thus keeping tissue homeostasis. However, the excessive or prolonged inflammation leads to tissue damage and organ dysfunction, such as pneumonia, hepatitis, nephritis, arthritis, etc. Usually, the process of inflammation includes local tissue injury, oozy and tissue hyperplasia. The skin, as the first line of host defense, interfaces with the environment and is exposed to a myriad of microorganisms. Thereby, skin inflammation is usually triggered by external stimulus, including inflammation of psoriasis, atopic dermatitis, neurodermatitis, etc. The etiology of these types of skin diseases is very complex and these diseases are hardly to be cured. Even though these diseases are cured, they are easily recurred.

Lipopeptides consist of a hydrophilic peptide chain and a lipophilicaliphatic chain, that is, about 10 peptides and aliphatic chain form a circular or linear lipopeptide. Lipopeptides are generally produced by Gram-positive bacteria and exhibit a variety of biological activities. Accumulating evidence shows that lipopeptides can function as surfactants, fungicides or insecticides. Moreover, it has been reported that a subclass of acylated lipopeptides have anti-inflammatory function (Long. E M, et al. A subclass of acylated anti-inflammaroty mediators usurp Toll-like receptor 2 to inhibit neutrophil recruitment through peroxisome proliferator activated receptor gamma. PNAS, 2011, 108(39):16357-62). However, beside the above lipopeptides, no other lipopeptide with anti-inflammatory activity has been identified. Therefore, it will be a promising field of bio-pharmacy.

Staphylococcus epidermidis, as one of most common commensal bacterial species, normally resides on the surface of the skin. Staphylococcus epidermidis produces many kinds of antibacterial molecules, including Pep5, PSMs, etc. All these peptides have anti-microbial activity. Besides antibacterial molecules, lipoteichoic acid (LTA), a product of staphylococci, has shown an anti-inflammatory effect on inhibiting TLR3-dependent inflammation after skin injury (LaiY, et al. Commensal bacteria regulate Toll-like receptor 3-dependent inflammation after skin injury. Nat Med. 2009, 15(12):1377-82.). However, whether lipopeptides produced by Staphylococcus epidermal have the anti-inflammatory activity remains unknown.

The present invention provides a novel anti-inflammatory lipopeptide which can suppress the inflammatory responses induced by poly(I:C), prevent the inflammation in wounds after skin injury, and alleviate inflammatory responses of skin inflammatory diseases such as allergic dermatitis.

SUMMARY OF THE INVENTION

The present invention provides a novel lipopeptide used for anti-inflammation, preparation methods and application thereof. The lipopeptide synthesized by using solid phase chemical synthesis is used to suppress inflammatory response induced by poly(I:C), to prevent inflammation in wounds after skin injury, and to alleviate inflammatory responses of skin inflammatory diseases such as allergic dermatitis.

One object of said invention is to provide an anti-inflammatory peptide, wherein, comprising of a peptide chain and aliphatic chain; the peptide chain being linked to the aliphatic chain through a peptide bond, and the aliphatic acid being linked to the N-terminus of the peptide chain; having a linear structure as Formula (1):

Formula (1) SEQ ID NO: 1

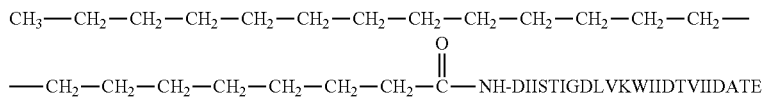

The second object of said invention is to provide a preparation method of the anti-inflammatory lipopeptide, wherein the peptide chain synthesized by using solid phase chemical synthesis is linked to the aliphatic chains through Phthalhydrazideoctyl ester and N-methyl morpholine.

The present invention further provides an use of the lipopeptide in the inhibition of the inflammatory response induced by poly(I:C). The in vitro experiments showed that poly (1:0) induced dramatically the expression of TNF-α and IL-6. The expression of inflammatory cytokines induced by poly (1:0) has been suppressed by said lipopeptide. The in vivo experiments also showed that the expression of mTNF-α and mIL-6 induced by poly(I:C) was significantly suppressed by said lipopeptide.

The present invention provides the anti-inflammatory lipopeptide binds to TLR2 on the surface of cell during the process of suppressing the inflammation.

In present invention, both wild type ($Tlr2^{+/+}$) and Tlr2 knockout ($Tlr2^{-/-}$) mice were used to detect the inhibitory effect of lipopeptide on the inflammation induced by poly (I:C). The results show that in $Tlr2^{+/+}$ mice the inflammation induced by poly (1:0) was significantly suppressed, as the expression of mTNF-α and mIL-6 was significantly inhibited by said lipopeptide. In Tlr2-deficient mice the lipopeptide failed to inhibit the inflammation. The results demonstrate that the inhibitory effect of said lipopeptide is dependent on TLR2.

In present invention, keratinocytes (MKC) isolated from wild type (Tlr2$^{+/+}$) and Tlr2 knockout (Tlr2$^{-/-}$) mice, were used to detect the inhibitory effect of said lipopeptide on poly (I:C)-induced inflammation. The lipopeptide significantly suppressed the expression of mTNF-α and mIL-6 induced by poly(I:C) in the keratinocytes from (Tlr2'+) mice, while the lipopeptide failed to inhibit the expression of mTNF-α and mIL-6 induced by poly(I:C) in the keratinocytes from Tlr2-deficient (Tlr2'$^-$) mice.

The present invention provides therapeutic application of the lipopeptide to develop drugs that can be used to suppress the inflammation in skin wounds. The lipopeptide inhibits the excessive inflammation in skin wounds.

Normally, mTNF-α and mIL-6 expression is increased significantly in wounds after skin injury. In present invention the experiment showed that the lipopeptide significantly decreased the expression of mTNF-α and mIL-6 in skin wounds. The lipopeptide suppressed the inflammatory responses in skin wounds, thus keeping tissue homeostasis and accelerating wound healing.

The present invention provides the application of said lipopeptide in the treatment with atopic dermatitis. The lipopeptide inhibits DNFB-induced inflammation.

Dinitrofluorobenzene (DNFB) was used to induced atopic dermatitis on the ear of the BALB/c mouse. DNFB significantly increased the expression of mTNF-α, mIL-4 and mIL-6 in mouse ears. The administration of the lipopeptide significantly inhibited DNFB-induced mIL-4 and mIL-6, thus alleviating inflammation in atopic dermatitis.

The present invention provides the application of said lipopeptide in the development of drugs that are used to inhibit the inflammation in skin wounds, as well as the inflammation of atopic dermatitis.

To mimics the condition of atopic dermatitis keratinocytes was stimulated by ovalbumin (OVA). To test the inhibitory effect of the lipopeptide on inflammatory response in atopic dermatitis, PBS, OVA, lipopeptide, lipopeptide plus OVA were used to stimulate keratinocytes (NHEK) and RNA was extracted after 24-hour stimulation. The expression of TNF-α and IL-6 was analyzed by real-time RT-PCR. The results showed that OVA enhanced the expression of TNF-α in NHEKs, while the lipopeptide inhibits TNF-α expression induced by OVA. Furthermore, OVA-induced expression of inflammatory factor was significantly decreased after NHEKs were treated with the PPARγ inhibitor GW9662, and suggesting OVA-induced inflammation is dependent on the activation of PPARγ.

In present invention, the mechanism by which poly(I:C) induces inflammation is that poly(I:C) activates TLR3 to induce p65 phosphorylation and translocation into nucleus, and then p65 interacts with PPARγ to promote TNF-α and IL-6 expression.

In present invention, the mechanism by which the lipopeptide inhibits poly(I:C)-induced inflammation is that the lipopeptide binds to TLR2 receptor, induces β-catenin phosphorylation (Tyr654) and enhances the stability of β-catenin, and then promotes β-catenin translocated into nucleus to interact with PPARγ, thus competing with poly(I:C)-induced p65. This competition decreases the interaction between p65 and PPARγ, thus inhibiting the inflammatory response.

In present invention, the anti-inflammatory lipopeptide can be synthesized by chemical methods. The lipopeptide can significantly inhibit poly (I:C)-induced inflammatory response, suppress the inflammation in the wounds, alleviate inflammatory response of atopic dermatitis. The mechanism is, the lipopeptide of present invention, by binding to TLR2 receptor, induces β-catenin translocation into nucleus to bind to PPARγ, which decreases the interaction between poly(I:C)-induced p65 with PPARγ, thereby inhibiting inflammatory responses.

DETAILED DESCRIPTION OF THE INVENTION

Example 1: The Synthesis of the Lipopeptide

The synthesis of the lipopeptide (Formula 1) was commissioned by GL biochem (Shanghai) Ltd., CHINA (www.glbiochem.com). The peptide chain of this lipopeptide which is synthesized by using solid phase chemical synthesis is linked to the aliphatic chain through Phthalhydrazideoctyl ester and N-methyl morpholine.

Formula (1) SEQ ID NO: 1

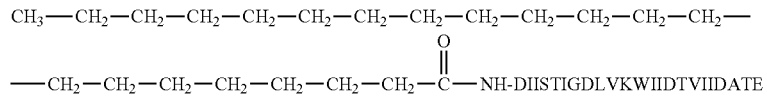

The above preparation method of solid phase chemical synthesis is FMOC (9-fluorenylmethyloxycarbonyl) synthesis method. The detailed protocol is:

1. Add the first amino acid and condensing agent into the activated Wang resin. Wash the resin by using detergent after the resin is oscillated for 2 hours.
2. Deprotect the FMOC of the first amino acid.
3. Add the second amino acid and condensing agent into the resin.
4. Repeat steps 2 and 3 until all amino acids are condensed.
5. Cleave the peptide from the resin. The cleavage agent is TFA:TIS:H$_2$O=25:1:1 (VN). The aliphatic chain is linked to peptide chain through Phthalhydrazideoctyl ester and N-methyl morpholine.
6. Purify the product with HPLC.

Figure 1:
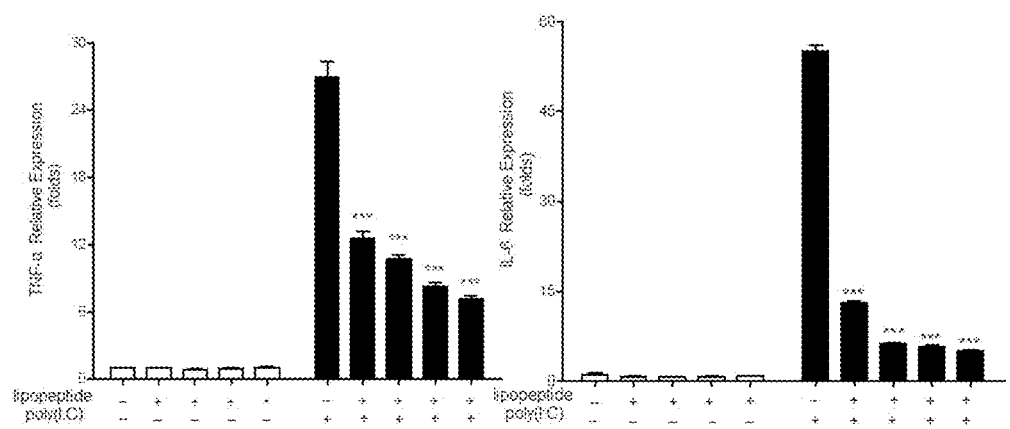
FIG. 1 shows the lipopeptide inhibits poly(I:C)-induced TNF-α and IL-6 expression hi NHEKs.

Example 2: The Lipopeptide Inhibits Poly(I:C)-Induced Inflammatory Response In Vitro NHEKs were seeded in 24-well plates to grow to 70~80% confluence, 2 ug/ml poly(I:C) were added. Different concentrations of the lipopeptide as Formula (1) in Example 1 were used to treat NHEKs. After 24 h, total RNA was extracted and cDNA was generated to detect the TNF-α and IL-6 expression by using real-time RT-PCR. As shown in FIG. 1, poly(I:C) dramatically induces TNF-α and IL-6 expression; after addition of the lipopeptide, the expression of TNF-α and IL-6 induced by poly(I:C) is suppressed by the lipopeptide.

Example 3: The Lipopeptide Inhibits Poly(I:C)-Induced Inflammation In Vivo

Figure 2:
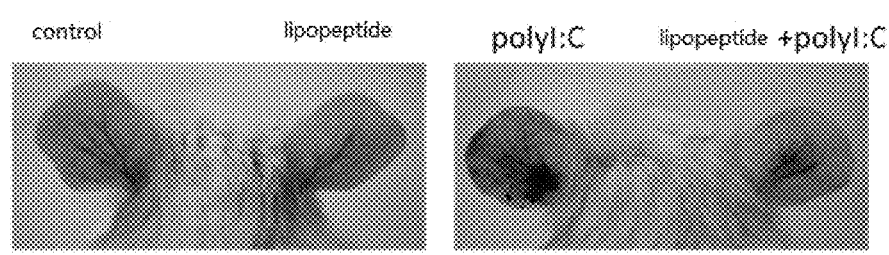
FIG. 2 shows in vivo the lipopeptide inhibits poly(I:C)-induced inflammatory response in mouse ears.
Figure 3:
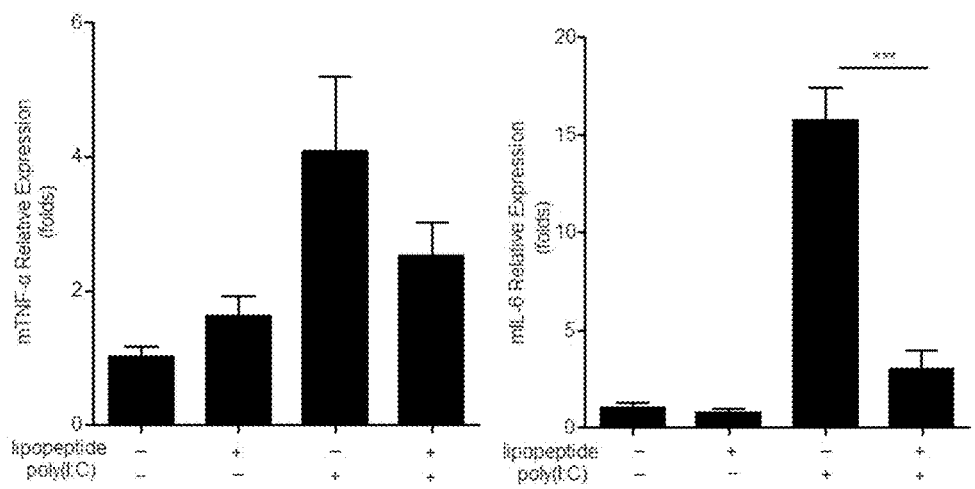
FIG. 3 shows vivo the lipopeptide inhibits poly(I:C)-induced mTNF-α and mIL-6 expression in mouse ears.
Figure 4:
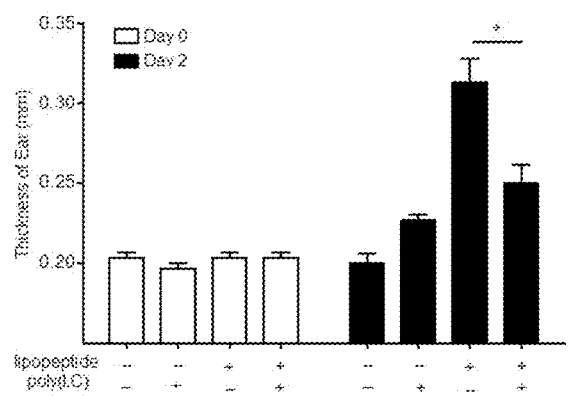
FIG. 4 shows the effect of the lipopeptide on poly(I:C)-induced ear thickness.

After BALB/c mice were anesthetized, 25 ug lipopeptide as Formula (1) in Example 1 or PBS was injected into the ear of BALB/c mice. 22 hours later, the ears were injected with the same amount of the lipopeptide as Formula (1) in Example 1 or PBS again. After full absorption of lipopeptide or PBS, 25 ug poly(I:C) was injected in each ear. Red swelling syndrome of ears was observed and photographed after 24 h. Ears were taken for RNA isolation to detect the expression of mTNF-α and mIL-6 or for H.E. staining. The results from FIG. 2 show that the ears with poly(I:C) injection exhibit increased swelling. The red swelling on ears was obviously alleviated after the injection of the lipopeptide. The experiment results from real-time RT-PCT show that the expression of mTNF-α and mIL-6 is significantly suppressed by the lipopeptide, as shown in FIG. 3. As shown in FIG. 4, after the injection of the lipopeptide, the ear thickness is significantly thinner, and white blood cells are decreased dramatically.

Example 4: Poly(I:C)-Induced Inflammation is Dependent on NFκB and PPAR-γ

Figure 5:
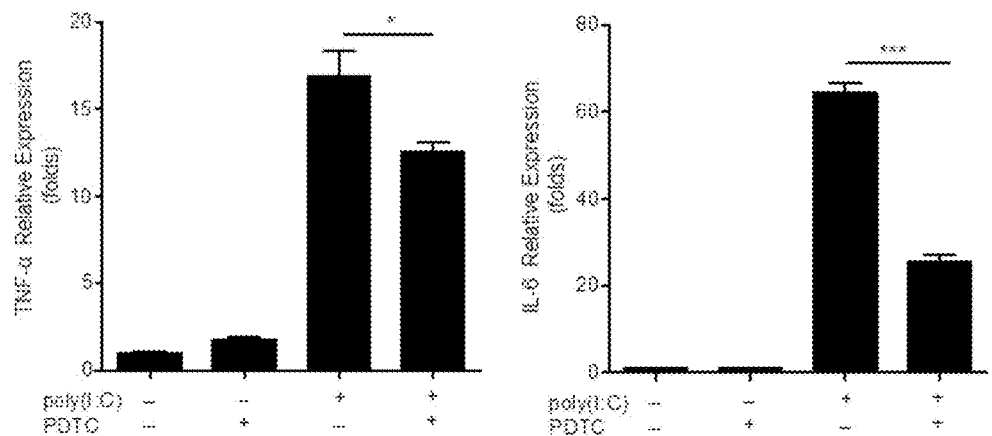
FIG. 5 shows NF-κB inhibitor-PDTC inhibits poly(I:C)-induced TNF-α and IL-6 expression in NHEKs.

NHEKs were treated with PBS, poly(I:C) with or without NFκB inhibitor PDTC, respectively. After 24 hours, total RNA was extracted and cDNA was generated to detect the expression of TNF-α and IL-6 by using real-time RT-PCR. The results from FIG. 5 show that poly(I:C) dramatically increases TNF-α and IL-6 mRNA expression. After addition of the PDTC, TNF-α and IL-6 mRNA expression is inhibited by PDTC. Thus these data demonstrate that poly(I:C) induces inflammatory response via the activation NF-κB.

Figure 6:
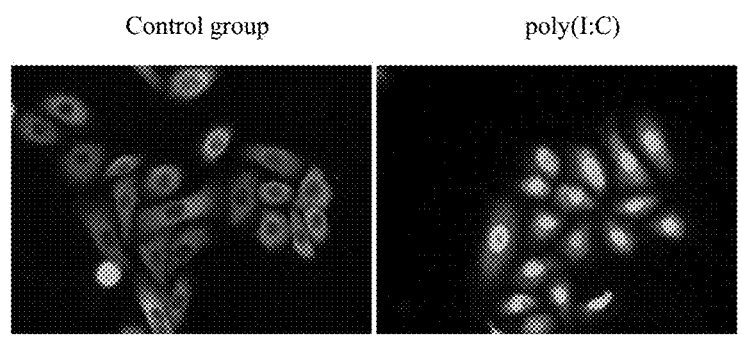
FIG. 6 shows poly(I:C) induces p65 translocation into nucleus.

NHEKs were treated with PBS or poly(I:C) for 4 hours, and fixed with formaldehyde for 15 min followed by adding ice-cold 0.25% TritonX-100 and hydrogen peroxide. Cells were incubated with anti-p65 antibody at 4° C. for overnight after blocked with BSA for 0.5 hour. Next day, the cells were incubated with the second antibody (FITC-goat anti Rabbit IgG) and visualized under the microscope. The results shown in FIG. 6 illustrate that poly(I:C) obviously induces p65 translocation into the nucleus, but no translocation is observed in control group.

Figure 7:
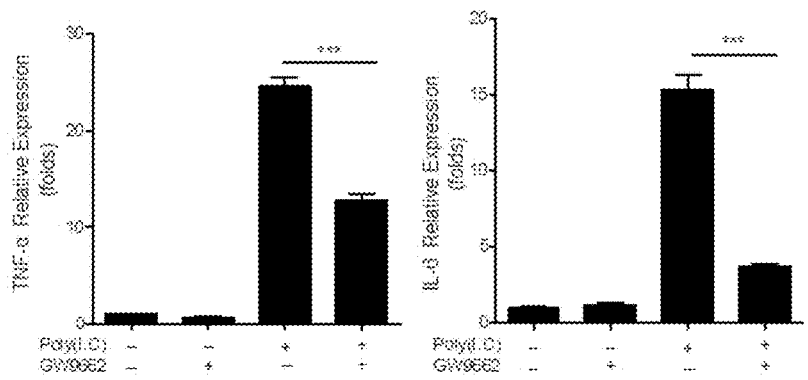
FIG. 7 shows PPAR-γ inhibitor-C' 9662 inhibits poly(I:C)-induced TNF-α and IL-6 expression.

NHEKs were treated with PBS, poly(I:C), PPAR-γ inhibitor GW9662, poly(I:C) with PPAR-γ inhibitor GW9662, respectively. 24 hours later, total RNA was extracted and cDNA was generated to detect the TNF-α and IL-6 expression by using real-time RT-PCR. The results shown in FIG. 7 illustrate that poly(I:C) dramatically increases TNF-α and IL-6 expression. After addition of the PPAR-γ inhibitor GW9662, TNF-α and IL-6 expression is significantly inhibited by GW9662. The data demonstrates that poly(I:C) induces the expression of TNF-α and IL-6 through PPAR-γ.

Example 5: Poly(I:C) Induces the Interaction Between PPAR-γ and P65

Figure 8:
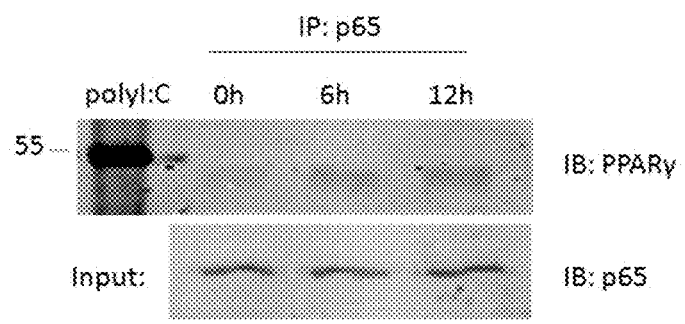
FIG. 8 shows poly(I:C) induces the interaction between PPAR-γ and p65.

Example 4 illustrates that poly(I:C) can induce p65 phosphorylation and translocation, and poly(I:C) induces the inflammatory response through PPAR-γ. The aim of Example 5 is to illustrate the interaction between the translocated p65 and PPAR-γ in the nucleus. NHEKs were treated with poly(I:C) for 4 hours or 12 hours. Whole-cell extracts were prepared by using lysis buffer containing NP40 and incubated with the p65 antibody at 4° C. for overnight. Protein AG beads were added and incubated at 4° C. for 1-2 hours. Beads were then washed twice with washing buffer. The immunoprecipitates were eluted with 20 ul 2× sodium dodecyl sulfate (SDS) loading buffer and separated by PAGE. The proteins were transferred to nitrocellulose membrane and probed with PPAR-γ antibody. The results shown in FIG. 8 illustrate that poly(I:C) significantly induces the interaction between PPAR-γ and P65, that is, poly(I:C) induces inflammatory response dependent on the combined effects of p65 and PPAR-γ.

Figure 9:
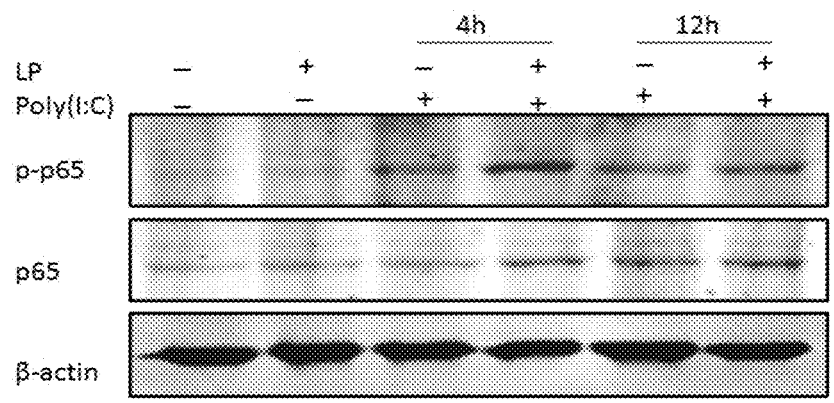
FIG. 9 shows the effects of the lipopeptide on poly(I:C)-induced p65 phosphorylation.

Example 6: The Lipopeptide does not Affect Poly(I:C)-Induced p65 Phosphorylation and Translocation NHEKs were treated with PBS, poly(I:C), lipopeptide, poly(I:C) with lipopeptide for 4 hours or 12 hours. And then RIPA lysate was added to lyse the cell. The protein concentration was detected by using BCA protein assay kit, and 40 ug of proteins were separated by SDS-PAGE. The effects of the lipopeptide on p65 phosphorylation were detected by Western blot. The results shown in FIG. 9 illustrate that at 4 hours and 12 hours, poly(I:C) significantly induces P65 phosphorylation, while the lipopeptide has no influence on p65 phosphorylation. Thus the data demonstrate that the lipopeptide inhibits the inflammatory response not by inhibiting p65 phosphorylation.

Figure 10:
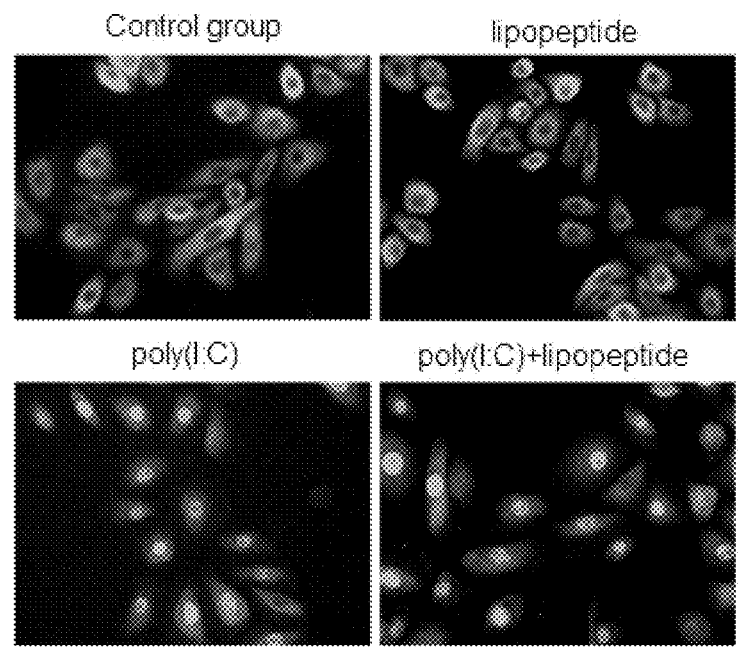
FIG. 10 shows the effects of the lipopeptide on poly(I:C)-induced p65 translocation (immunofluorescence).

NHEKs were treated with PBS, lipopeptide, poly(I:C) with or without lipopeptide for 12 hours, and fixed with formaldehyde for 15 min followed by adding ice-cold 0.25% TritonX-100 and hydrogen peroxide. Cells were stained with anti-p65 antibody for overnight after blocked with BSA for 0.5 h. Then the cells were incubated with the second antibody (FITC-goat anti Rabbit IgG) and visualized under the microscope. The data shown in FIG. 10 illustrate that, compared with the controls, poly(I:C) obviously induces p65 translocation into the nucleus, but the lipopeptide has no effect on poly(I:C)-induced p65 translocation.

Figure 11:
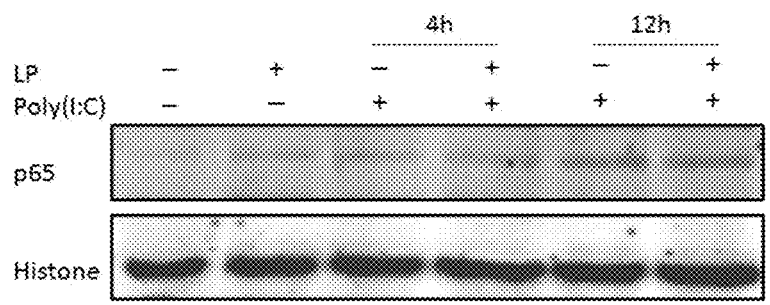
FIG. 11 shows the effects of the lipopeptide on poly(I:C)-induced p65 translocation (western blot).

NHEKs were treated with PBS, poly(I:C), lipopeptide, poly(I:C) with lipopeptide for 12 hours. Proteins from nucleus were isolated and separated by PAGE. The p65 in the nucleus was detected by Western blot. The results shown in FIG. 11 illustrate that poly(I:C) significantly increases the level of p65 in the nucleus, while the addition of the lipopeptide has no influence on the translocation of p65 into nucleus induced by poly(I:C). Thus the lipopeptide has no effect on poly(I:C)-induced p65 translocation into the nucleus.

In conclusion, the lipopeptide has no effect on poly(I:C)-induced p65 phosphorylation and/or p65 translocation; the suppression on the inflammatory response by the lipopeptide is not through inhibiting p65 phosphorylation and/or p65 translocation.

Example 7: The Inhibitory Effect of the Lipopeptide on Poly(I:C)-Induced Inflammatory Response is Dependent on TLR2

Wild type (Tlr2$^{+/+}$) and Tlr2 knockout (Tlr2$^{-/-}$) mice were used to detect the inhibitory effect of the lipopeptide on poly (1:0)-induced inflammation.

Figure 12:
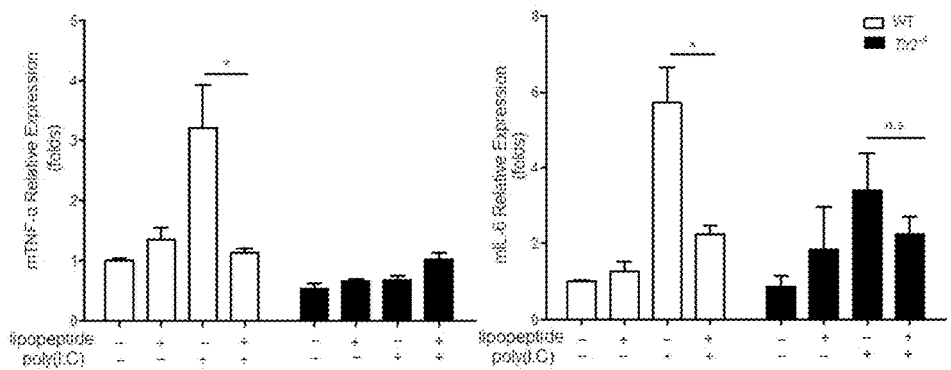
FIG. 12 shows the effects of the lipopeptide on poly(I:C)-induced inflammatory response in Tlr2$^{+/+}$ mice and Tlr2$^{-/-}$ mice, respectively.

After wild type (Tlr2$^{+/+}$) C57BL/6 mice and Tlr2 knockout (Tlr2$^{-/-}$) mice were anesthetized, 25 ug lipopeptide or PBS were injected into the ears of wild type (Tlr2$^{+/+}$) and Tlr2 knockout (Tlr2$^{t-/-}$) mice. 22 hours later, the same amount of the lipopeptide or PBS was injected into the ears again. After the lipopeptide or PBS was fully absorbed, 25 ug poly (1:0) was injected into each ear. Red swelling of ears was observed and photographed after 24 h. To detect the expression of mTNF-α and mIL-6 ears were taken for RNA extraction. The results shown in FIG. 12 illustrate that the lipopeptide inhibits poly(I:C)-induced mTNF-α and mIL-6 expression in wild-type (Tlr2$^{+/+}$) C57BL/6 mice, that is, the lipopeptide significantly inhibits poly(I:C)-induced inflammation. However, the lipopeptide has no effect on inhibiting poly(I:C)-induced inflammation in Tlr2 knockout (Tlr2$^{-/-}$) mice.

Figure 13:
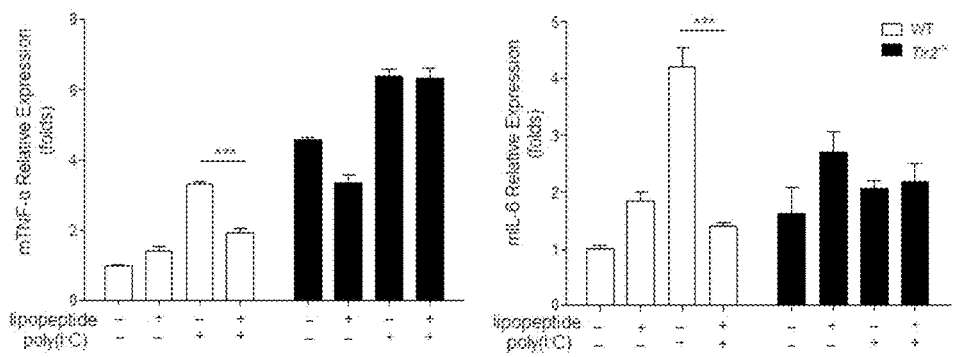
FIG. 13 shows the effects of the lipopeptide on poly(I:C)-induced inflammatory response on keratinocyte from Tlr2$^{+/+}$ mice and Tlr2$^{-/-}$ mice, respectively.

Keratinocytes isolated from wild type (Tlr2$^{+/+}$) and Tlr2 knockout (Tlr2$^{-/-}$) mice were treated with PBS, poly(I:C), the lipopeptide, poly(I:C) and the lipopeptide. 24 hours later, total RNA was extracted and cDNA was generated to detect TNF-α and IL-6 expression. The result from FIG. 13 shows that the lipopeptide inhibits poly(I:C)-induced TNF-α and IL-6 expression in keratinocytes from wild type (Tlr2$^{+/+}$) mice but not in keratinocytes from Tlr2 knockout mice. In conclusion, the inhibitory effect of the lipopeptide on poly (I:C)-induced inflammation is dependent on TLR2.

Example 8: The Lipopeptide Induces β-Catenin Phosphorylation and Translocation

Figure 14:
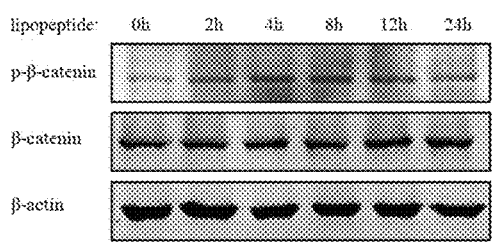
FIG. 14 shows the effects of the lipopeptide on β-catenin phosphorylation (Tyr654).
Figure 15:
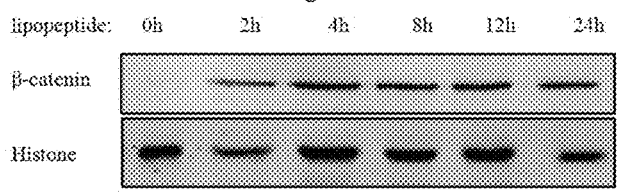
FIG. 15 shows the lipopeptide induces β-catenin translocation into the nucleus (nucleocytoplasmic separation).

NHEKs were treated with 6 ug/ml the lipopeptide for 0, 2, 4, 8, 12, 24 hours. Whole-cell extracts were prepared by using RIPA buffer and proteins (40 ug) were separated by PAGE. The β-catenin phosphorylation was detected by Western blot. The results shown in FIG. 14 illustrate that the lipopeptide induces the phosphorylation of β-catenin at Tyr654. It has been reported that the phosphorylation at Tyr654 enhances the stability of β-catenin and further promotes β-catenin translocation into nucleus. On the other hand, as shown in FIG. 15, nuclear proteins were isolated from NHEKs treated with 6 ug/ml the lipopeptide for various times was detected by western blot. The results show that the lipopeptide significantly promotes β-catenin translocation into the nucleus in NHEKs.

Figure 16:
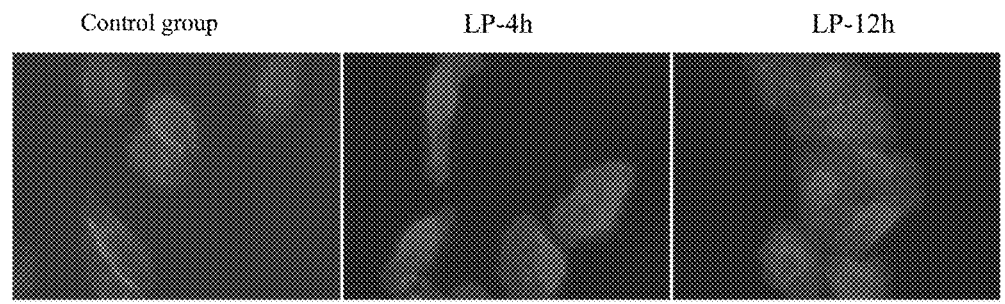
FIG. 16 shows the lipopeptide induces β-catenin translocation by using immunofluorescent staining.

Furthermore, NHEKs were treated with PBS, the lipopeptide for 12 h and fixed with formaldehyde for 15 min followed by adding ice-cold 0.25% TritonX-100 and hydrogen peroxide. Cells were incubated with β-catenin antibody at 4° C. for overnight after blocked with BSA for 0.5 h. Then the cells were incubated with the second antibody (FITC-goat anti Rabbit IgG) and visualized under the microscope. The results shown in FIG. 16 illustrate that the lipopeptide promotes β-catenin translocation into the nucleus, while the β-catenin stays outside the nucleus in control group.

In conclusion, the lipopeptide induces the phosphorylation of β-catenin at Tyr654 to enhance its stability, and then promotes β-catenin translocation into the nucleus.

Figure 17:
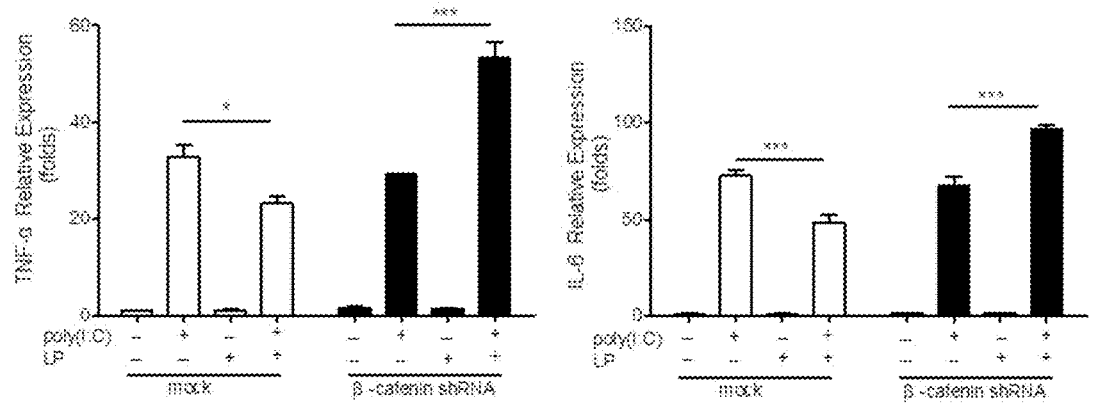
FIG. 17 shows the inhibitory effect of the lipopeptide on poly(I:C)-induced inflammation is dependent on β-catenin.

Example 9: The Inhibitory Effect of the Lipopeptide on Poly(I:C)-Induced Inflammatory Response is Dependent on β-Catenin Example 8 illustrates that lipopeptide promotes β-catenin phosphorylation and further promotes β-catenin translocation. In Example 9, to figure out whether the lipopeptide can suppress the inflammatory response induced by poly(I:C) or not, we used gene silencing to inhibit the expression of β-catenin gene. The experiment results show that the lipopeptide no longer inhibits the inflammatory response induced by poly(I:C) after β-catenin gene has been silenced, while the lipopeptide inhibits the inflammatory response induced by poly(I:C) in the control groups, as shown in FIG. 17. Therefore, the lipopeptide promotes β-catenin translocation into nucleus to inhibit the inflammatory response induced by poly(I:C). The lipopeptide does not inhibit the inflammatory response after β-catenin silencing.

Figure 18:
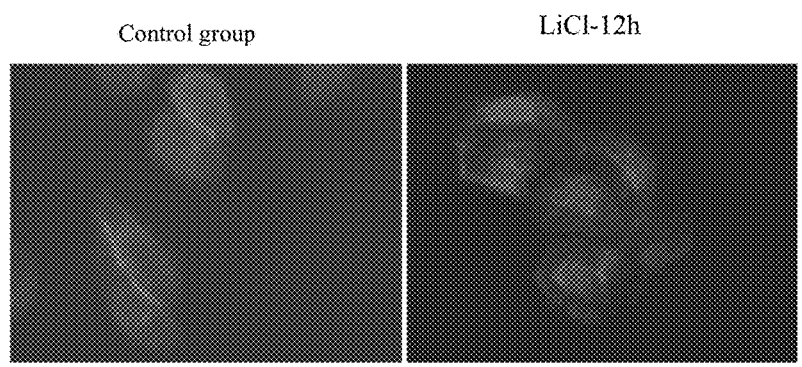
FIG. 18 shows LiCl induces β-catenin translocation (nucleocytoplasmic separation).
Figure 19:
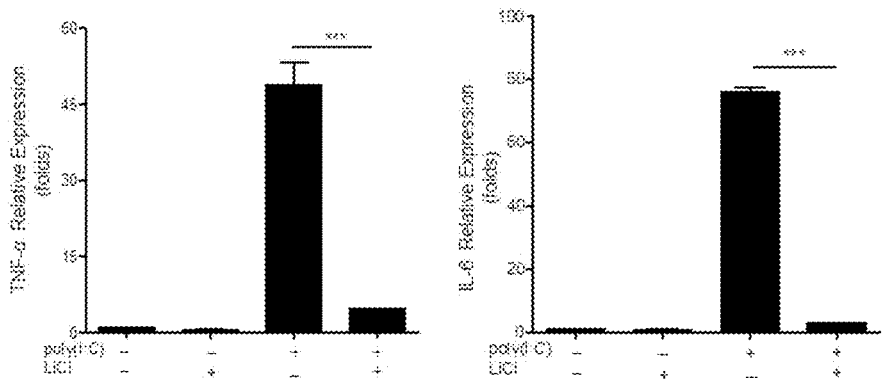
FIG. 19 shows LiCl inhibits poly(I:C)-induced inflammatory response.

LiCl is the inhibitor of GSK3β which leads to the degradation of β-catenin. It has been reported that LiCl induces β-catenin translocation in vascular smooth muscle cells. As disclosed in present invention, LiCl also induces β-catenin translocation in NHEKs, shown in FIG. 18. Example 8 illustrates that the lipopeptide promotes β-catenin translocation and LiCl promotes β-catenin translocation into the nucleus as well. We further determine the effects of LiCl on the inflammatory response induced by poly(I:C). NHEKs were treated with PBS, LiCl, poly(I:C), poly(I:C) with LiCl for 24 hours. The results shown in FIG. 19 illustrate that LiCl, as well as the lipopeptide, inhibits poly(I:C)-induced inflammatory response by real-time RT-PCR.

Figure 20:
FIG. 20 shows the lipopeptide induces the interaction between PPAR-γ and β-catenin.
Figure 21:
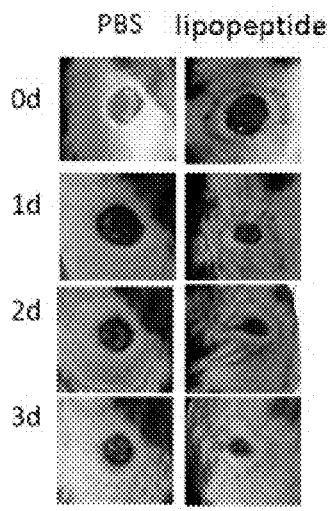
FIG. 21 shows the lipopeptide promotes the healing of skin wounds in mice.
Figure 22:
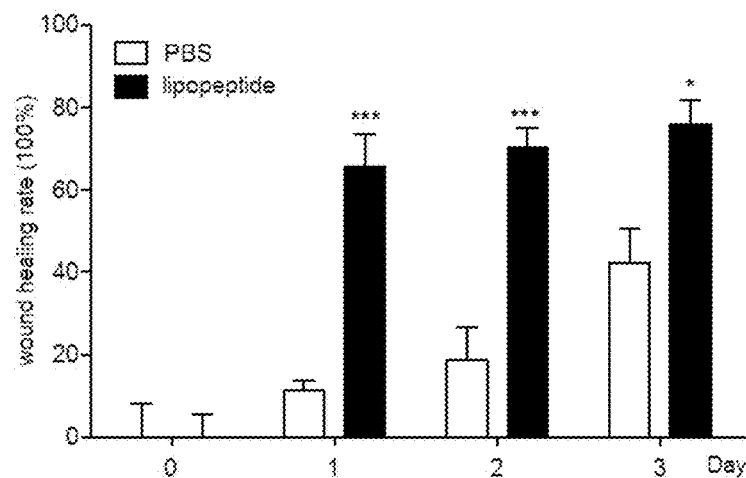
FIG. 22 shows the lipopeptide increases the healing rate of skin wounds in mice.
Figure 23:
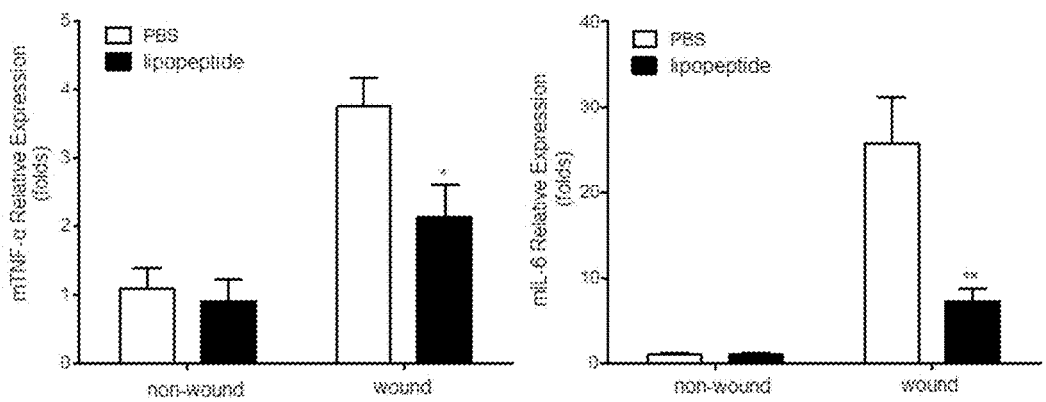
FIG. 23 shows the lipopeptide inhibits TNF-α and IL-6 expression in the wounds of mice.

Example 10: The Lipopeptide Induces the Interaction Between PPAR-γ and β-Catenin Example 4 illustrates the inflammatory response induced by poly(I:C) is dependent on PPAR-γ, which is a transcription factor in the nucleus. Example 8 illustrates that the lipopeptide promotes β-catenin translocation into the nucleus. To determine the interaction between PPAR-γ and β-catenin, NHEKs were treated with lipopeptide for 12 h. Whole-cell extracts were prepared by using lysis buffer containing NP40 and incubated with the β-catenin antibody at 4° C. for overnight. Protein AG beads were added and the incubation was continued at 4° C. for 1-2 h. Beads were then washed twice with washing buffer. And then immunoprecipitates were eluted with 20 ul 2× sodium dodecyl sulfate (SDS) loading buffer and separated by PAGE. The results shown in FIG. 20 illustrate that the lipopeptide markedly induces the interaction between PPAR-γ and β-catenin. Thereby the suppressive effect of the lipopeptide on inflammatory response can be achieved by promoting the interaction between PPAR-γ and β-catenin.

shown in FIG. 21-22 illustrate that the injection of the lipopeptide decreases the inflammatory response in the wound area and thus markedly accelerates wound healing. As shown in FIG. 23, the promotion of wound healing by the lipopeptide can be achieved by inhibiting the excessive inflammatory response in the wound area.

Figure 24:
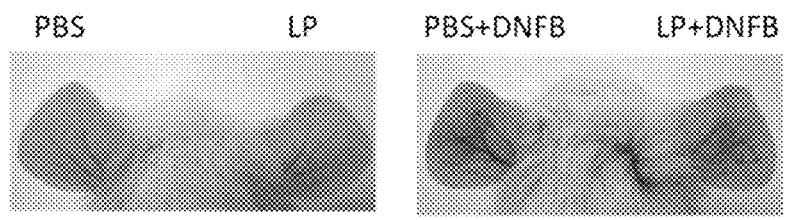
FIG. 24 shows the effects of the lipopeptide on DNFB-induced atopic dermatitis of mice ears.
Figure 25:
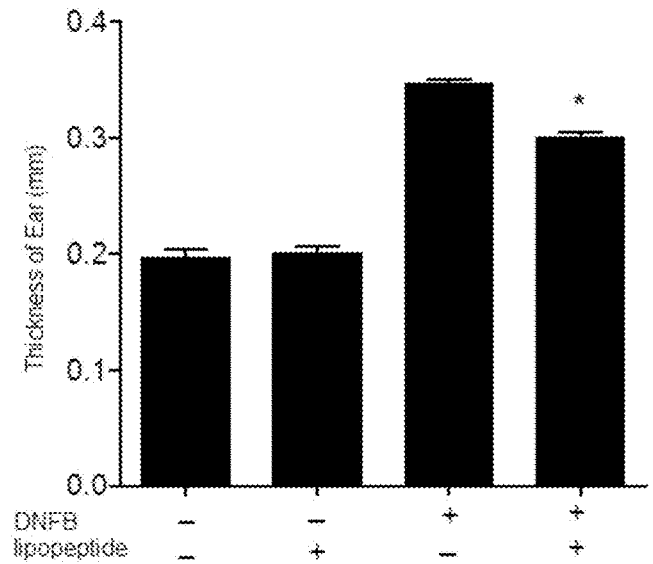
FIG. 25 shows the effects of the lipopeptide on DNFB-increased ear thickness in mice.
Figure 26:
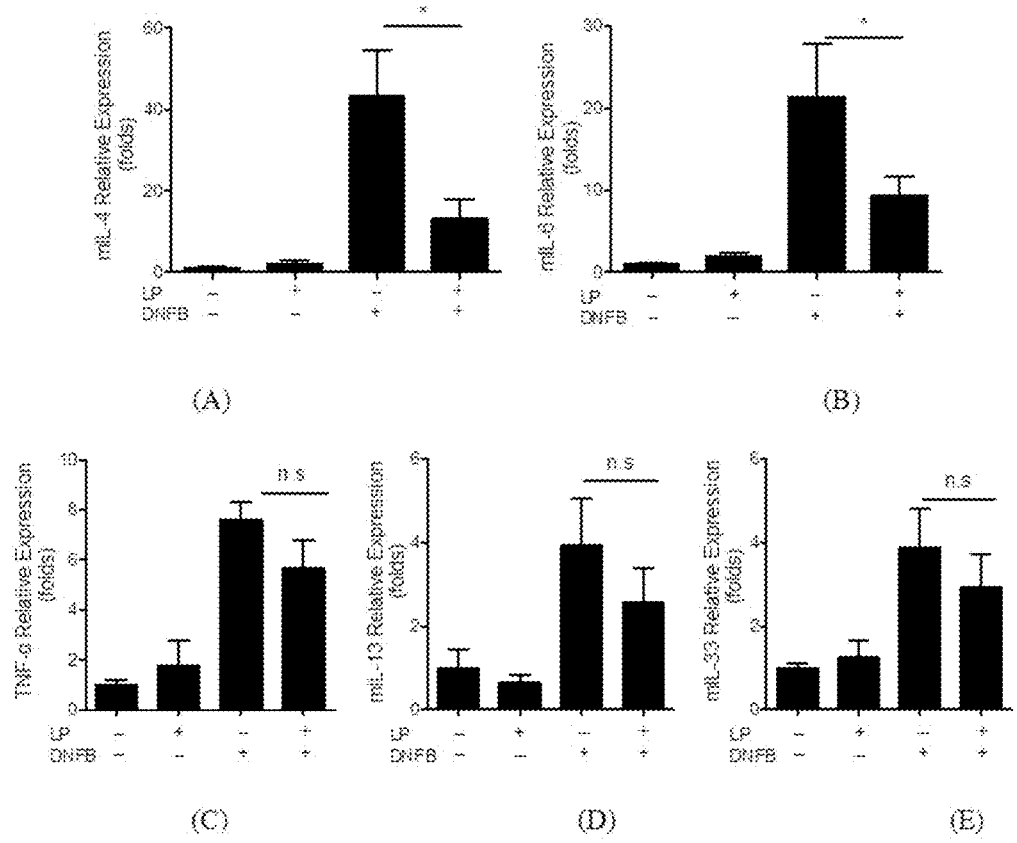
FIG. 26 shows the effects of the lipopeptide on inflammatory factors of DNFB-induced atopic dermatitis of mice ears.

Example 12: The Lipopeptide Suppresses Inflammatory Response in Atopic Dermatitis The hair on the abdomen of BALB/c adult mice was shaved and was topically applied with 100 ug dinitrofluorobenzene (DNFB, 5 mg/ml) for twice. DNFB is dissolved in the mixture of acetone and olive oil (V/V=4/1). After 5 days, 25 ug the lipopeptide or PBS was injected into the ears of the mice. After 22 hours, the same amount of the lipopeptide or PBS was injected into the ears again. After the lipopeptide or PBS was fully absorbed, 25 ug DNFB (2 mg/ml) was topically applied on each ear. 2 day later, the thickness of each ear was measured, and was taken either for RNA isolation to detect the expression of mTNF-α, mIL-6, mIL-4, mIL-13, mIL-33 by real-time RT-PCR, or for H&E staining. The results shown in FIG. 24 illustrate that DNFB induces atopic dermatitis on mouse ears. Red swelling can be observed obviously. The red swelling is alleviated and the ear thickness becomes thinner after the lipopeptide treatment, shown in FIG. 25. Furthermore, DNFB significantly induces the expression of mTNF-α, mIL-4 and mIL-6. The increased expression of mIL-4 and mIL-6 (P<0.05) are significantly inhibited by the lipopeptide, shown in FIG. 26(A-B). Moreover, the expression of mTNF-α, mIL-13, mIL-33 (P<0.05) are inhibited by the lipopeptide, shown in FIG. 26(C-E).

---

SEQUENCE LISTING

<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide

<400> SEQUENCE: 1

Asp Ile Ile Ser Thr Ile Gly Asp Leu Val Lys Trp Ile Ile Asp Thr
1               5                   10                  15

Val Ile Ile Asp Ala Thr Glu
            20

---

Example 11: The Lipopeptide Suppresses Inflammation in Skin Wounds and Promotes Wound Healing The above examples illustrate the lipopeptide suppresses the inflammation induced by poly(I:C) in vitro or in vivo. Example 11 further verifies that the lipopeptide suppresses the inflammation in skin wounds. The hair on the backs of C57BL/6 adult mice was shaved and removed by chemical depilation. 50 μg of the lipopeptide as Formula (1) was intradermally injected into mouse back skin 24 hours before wounding. 8 mm wounds were made by biopsy punches and wound areas were photographed every day. 3 days later, 2 mm of skin around wound edges or unwounded skin were taken either for RNA isolation or H&E staining. The results

What is claimed is:

1. An anti-inflammatory lipopeptide comprising a peptide chain and an aliphatic chain; the peptide chain being linked to the aliphatic chain through a peptide bond, and the aliphatic chain being linked to the N-terminus of the peptide chain; said lipopeptide having the structure as the Formula (1);

Formula (1) SEQ ID NO: 1

$CH_3-CH_2-CH_2-CH_2-CH_2-CH_2-CH_2-CH_2-CH_2-$
$-CH_2-CH_2-CH_2-CH_2-CH_2-CH_2-CH_2-CH_2-$

-continued

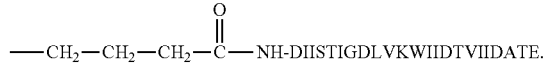

2. A method of suppressing inflammatory response induced by poly(I:C), which comprises administering the anti-inflammatory lipopeptide according to claim 1.

3. A method of suppressing inflammatory responses induced by dinitrofluorobenzene (DNFB), which comprises administering the anti-inflammatory lipopeptide according to claim 1.

4. A composition for inhibiting inflammation in wounds which comprises the anti-inflammatory lipopeptide according to claim 1.

5. A composition for treating atopic dermatitis, which comprises anti-inflammatory lipopeptide according to claim 1.

6. A method of inhibiting an inflammatory response, which comprises administering to patient in need thereof an effective amount of the anti-inflammatory lipopeptide according to claim 1, wherein, the lipopeptide binds to TLR2, induces β-catenin translocation into nucleus, and then β-catenin competes with p65 for interaction with PPARγ, thus inhibiting inflammatory response.

* * * * *